United States Patent
Kris et al.

(10) Patent No.: US 9,610,137 B1
(45) Date of Patent: Apr. 4, 2017

(54) DENTAL WORK SITE ILLUMINATION SYSTEM

(71) Applicants: Gary S. Kris, White Plains, NY (US); Stanley Zhao, Dalian (CN)

(72) Inventors: Gary S. Kris, White Plains, NY (US); Stanley Zhao, Dalian (CN)

(73) Assignee: Promident LLC, Valley Cottage, NY (US)

( * ) Notice: Subject to any disclaimer, the term of this patent is extended or adjusted under 35 U.S.C. 154(b) by 161 days.

(21) Appl. No.: 14/557,764

(22) Filed: Dec. 2, 2014

(51) Int. Cl.
*A61C 1/05* (2006.01)
*A61C 1/08* (2006.01)
*A61C 1/10* (2006.01)
*A61C 1/12* (2006.01)

(52) U.S. Cl.
CPC .............. *A61C 1/088* (2013.01); *A61C 1/05* (2013.01); *A61C 1/082* (2013.01); *A61C 1/10* (2013.01); *A61C 1/12* (2013.01)

(58) Field of Classification Search
CPC .......... A61C 1/088; A61C 1/05; A61C 1/082; A61C 1/10; A61C 1/12

USPC ................. 433/132, 103, 114, 120
See application file for complete search history.

(56) References Cited

U.S. PATENT DOCUMENTS

| | | | | |
|---|---|---|---|---|
| 2008/0145817 A1* | 6/2008 | Brennan | ............... | A61C 1/003 433/98 |
| 2008/0261172 A1* | 10/2008 | Rauchenzauner | ....... | A61C 1/05 433/132 |
| 2012/0111590 A1* | 5/2012 | Rothenwaender | ..... | A61C 1/003 173/15 |

* cited by examiner

*Primary Examiner* — Michael Carey
(74) *Attorney, Agent, or Firm* — Michael R. Philips

(57) ABSTRACT

A dental work site illumination system provides illumination directly onto a work site under professional dental care. The illumination emanates from a light source within the swivel coupling, the light source being energized by an electrical generator mounted within the coupling. The generator is driven by a turbine wheel that is caused to rotate by a flow of exhaust fluid, i.e. compressed fluid after having driven a dental tool. The light source transmits illumination to a fiber optic bundle that terminates adjacent to the dental work site.

20 Claims, 2 Drawing Sheets

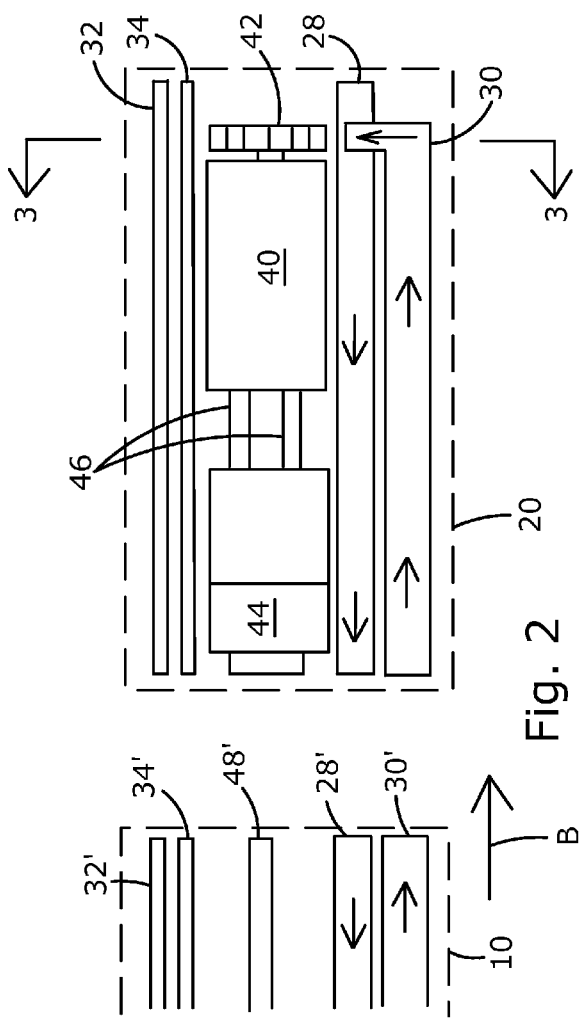
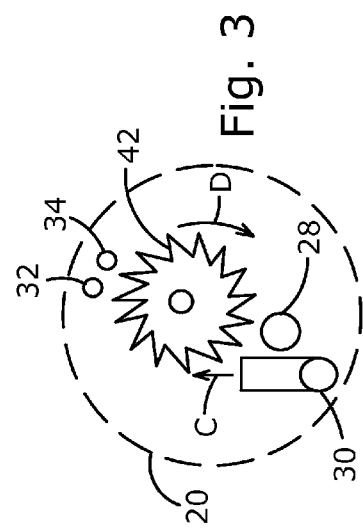

DENTAL WORK SITE ILLUMINATION SYSTEM

FIELD OF THE INVENTION

The present invention relates to the field of dental equipment and more particularly to an apparatus for providing illumination in close proximity to the patient's teeth.

BACKGROUND OF THE INVENTION

It has been known that the overhead light used in traditional dental practice has inherent problems. The dentist works for periods of time with the dentist's hands, and possibly head, partially preventing the light from illuminating the work site inside of the patient's mouth. One improvement on this overhead lighting system that has been in use for several years is a light that is strapped to the dentist's forehead. While this "headlight" does bring the light closer to the work area and avoids interference by the dentist's head, the dentist's hands continue to block the light at the work site.

Pursuant to the development of fiber optic filaments for the transmission of light, a remote light source was introduced to bring illumination to the tip of the dental handpiece, improving visibility in the work area. This system uses a light source that is typically located in the dental chair or an instrument panel. The entry end of the fiber optic bundle is positioned adjacent to the light source and the fiber optic filaments travel through the supply hose through a swivel coupling to bring light into the handpiece at a point that is close to the drill bit. In an alternate design, the light source is located in the swivel coupling with electric current being supplied from the dental chair or instrument panel through a set of wires enclosed in the supply hose. This newer system is quite effective in providing illumination at the work site with virtually no blockage by the dentist's head or hands. However, the need for long fiber optic filaments or electric wires and their associated weight as well as a control box/transformer and access to electricity makes this lighting system expensive and cumbersome. Furthermore, installing and servicing this existing lighting system requires significant expertise and time.

Most rotary dental apparatus is driven by a flow of compressed air that travels through the supply hose and through the swivel coupling to the handpiece. The swivel coupling serves to connect the supply hose to the handpiece, transmitting compressed air and water while allowing the handpiece to be rotated to access various surfaces of the patient's teeth. After the compressed air passes through the handpiece, the air is discharged.

SUMMARY OF THE INVENTION

The present invention provides a unique dental work site illumination system that overcomes the drawbacks of the previously known dental lighting systems. A turbine wheel mounted within the swivel coupling is driven by the compressed air after driving the dental tool. The driven turbine wheel rotates a miniature generator to create an electric current that is connected to a light source located adjacent to the distal end of the swivel coupling. A receptor end of a fiber optic bundle housed within the handpiece is positioned adjacent to the light source, the delivery end of the fiber optic bundle being positioned adjacent to the drill bit. The light transmitted along the fiber optic bundle illuminates the dental work site at close range.

BRIEF DESCRIPTION OF THE DRAWINGS

The present invention is best understood in conjunction with the accompanying drawing figures in which like elements are identified by similar reference numerals and wherein:

FIG. 2 is a schematic cross sectional view of the swivel coupling according to the invention with a proximal end of a dental handpiece positioned for attachment to the swivel coupling.

FIG. 3 is a schematic cross sectional view taken in the direction of line 3-3 of FIG. 2.

DETAILED DESCRIPTION OF THE PREFERRED EMBODIMENT

Figure 1:
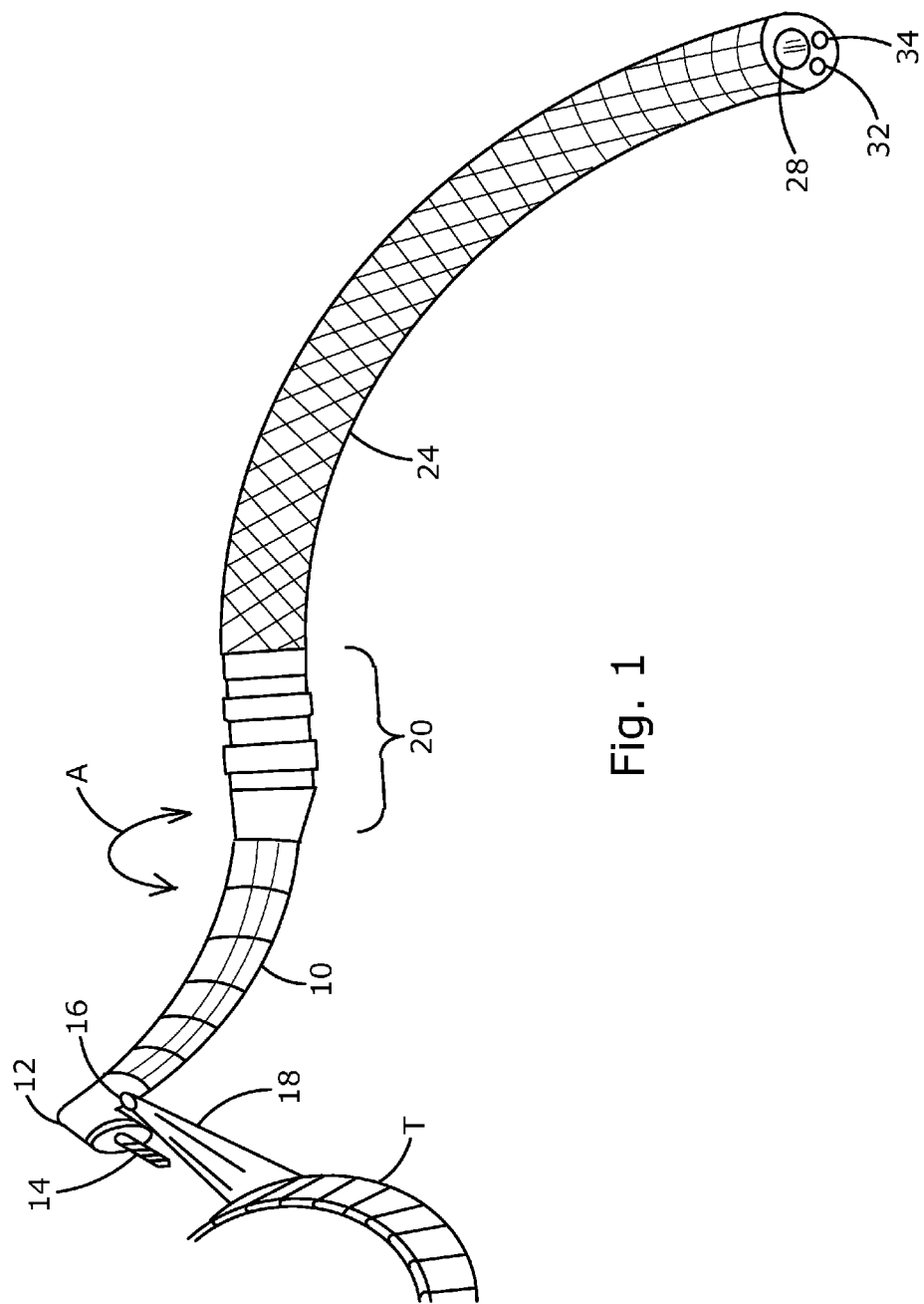
FIG. 1 is a perspective view of a dental handpiece mounted to a swivel coupling at the end of a supply hose, the dental handpiece incorporating a fiber optic lens with a light beam emanating therefrom.

Referring to FIG. 1, a dental handpiece 10 is illustrated in schematic perspective view as being mounted to a coupling component 20 that is fixedly connected to a flexible supply hose 24, dental handpiece 10 being positioned adjacent to a set of teeth T. As used herein, the term "dental work site" is defined to identify an area of the patient's teeth being professionally treated. Coupling component 20 is preferably configured to swivel, allowing the dentist or dental technician using the dental equipment to rotate handpiece 10 in the direction indicated by arrow A for greater control and comfort. Handpiece 10 is easily mounted to or removed from swivel coupling 20 through a snap connector, as is known. Handpiece 10 has a chuck 12 at a distal end thereof with a drill bit 14 mounted in chuck 12. A lens 16 is mounted adjacent to chuck 12 and drill bit 14. Lens 16 is the light delivery end of a fiber optic bundle (not visible) contained within handpiece 10. A light beam 18 is directed from lens 16 to illuminate a work site area on the surface of teeth T.

Continuing with reference to FIG. 1, swivel coupling 20 is assembled to the output end of supply hose 24. Supply hose 24 is a highly flexible conduit including a pressurized supply tube 28 for delivery of compressed air or another compressed fluid that is used to drive drill bit 14 at a high rate of speed. In addition, a water tube 32 and a chip air tube 34 are contained in supply hose 24. Water tube 32 provides cooling water to protect drill bit 14, and chip air tube 34 atomizes the water flowing from water tube 32, as is known. It is particularly noted that there is no fiber optic bundle or electric wires included in supply hose 24.

Referring now to FIG. 2, a schematic side cross sectional view of swivel coupling 20 is shown adjacent to an end portion of handpiece 10 that is positioned for being moved in the direction indicated by arrow B to be connected to swivel coupling 20. Certain mechanical details of swivel coupling 20 that are currently known are not shown for reasons of clarity, particularly the swivel mechanism and the snap connector. The housing of swivel coupling 20 is shown in dashed lines. As illustrated, the right end of swivel coupling 20 is configured for assembly to supply hose 24 (see FIG. 1). A pressurized supply tube 28, a water tube 32 and a chip air tube 34 are shown at the right end of swivel coupling 20 in positions to engage respective ends of mating tubing within the supply hose. The opposite ends of pressurized supply tube 28, water tube 32 and chip air tube 34 are located at the left end of swivel coupling 20 for connection to handpiece 10. A mating set of pressurized supply tube 28', water tube 32' and chip air tube 34' are situated within handpiece 10. Handpiece 10 is to be moved in the direction indicated by arrow B for connection to swivel coupling 20. During the use of dental handpiece 10, compressed air or other pressurized fluid is conveyed through pressurized supply tube 28 in swivel coupling 20 and through pressurized supply tube 28' in handpiece 10 to drive the connected drill bit or other tool. Subsequently the fluid, being somewhat pressure depleted, is conducted away. An exhaust tube 30' is provided within handpiece 10 to conduct used compressed fluid, now at a relatively low pressure, out of handpiece 10. Exhaust tube 30' connects to exhaust tube 30 within swivel coupling 20. Pressurized fluid, e.g. pressurized air, flows through supply tubes 28, 28' and through exhaust tubes 30', 30 in the directions indicated by flow arrows (not numbered). Near the end of swivel coupling 20 that is assembled to the supply hose, exhaust tube 30 is formed with a bend to direct the exhaust fluid toward a turbine wheel 42, causing turbine wheel 42 to rotate. The exhaust fluid is discharged to atmosphere or through tubing within supply hose 24 after rotating turbine wheel 42.

FIG. 3 provides a detailed view of turbine wheel 42 taken in the direction of line 3-3 of FIG. 2. Whereas driving a turbine wheel by the flow of compressed fluid is known, driving the turbine wheel with primary compressed fluid, before driving the rotary dental tool, results in a reduction of the force and effectiveness of tool rotation. Therefore, a preferred embodiment of the invention utilizes the exhaust fluid, i.e. fluid having a lower pressure after having driven the tool. Exhaust fluid is expelled from exhaust tube 30 in the direction indicated by arrow C to rotate turbine wheel 42 in the direction indicated by arrow D. Turbine wheel 42 is configured with a plurality of vanes, preferably oriented at an angle to the radii in order to obtain maximum drive force from the exhaust fluid. Therefore, by driving the turbine wheel with the exhaust fluid subsequent to driving the tool rotation, little or no reduction in tool drive power occurs. The preferred embodiment of the present invention is to rotationally drive the turbine wheel with exhaust fluid, particularly exhaust air.

Referring again to FIG. 2, turbine wheel 42 is mechanically coupled to an electrical generator 40 in a manner to activate generator 40 to generate an electric current. Electric generator 40 is manufactured of materials adapted to undergo repeated autoclave cycles. The electric current from generator 40 passes through wires 46 that are connected to a light source 44. Generator 40 is capable of providing sufficient power to drive light source 44. Generator 40 is sufficiently small and light weight to mount within swivel coupling 20 and sufficiently powerful to illuminate light source 44. A generator adapted to satisfy the requirements of the present invention is approximately 6.0 mm in diameter by 12.0 mm in length and is capable of producing 20 milliamps at 2.7 volts. According to the preferred embodiment of the invention, light source 44 is an LED light source with a power rating of 0.03-0.05 watts at 2.6-2.7 volts. However, alternate light source types are understood to be within the scope of the present invention. The light emanating from light source 44 is transmitted to a fiber optic bundle 48' positioned in the connective end of handpiece 10 when handpiece 10 is mounted to swivel coupling 20. Fiber optic bundle 48' transmits illumination to fiber optic lens 16 (see FIG. 1) to be in close proximity and directed to the dental work site for improved visibility by the dentist or technician.

While the description above discloses a preferred embodiment of the present invention, it is contemplated that numerous variations and modifications of the invention are possible and are considered to be within the scope of the claims that follow.

What is claimed is:

1. A dental work site illumination system, comprising:
   a. a coupling component fixedly assembled to a supply hose, the supply hose configured for conveying pressurized fluid to the coupling component;
   b. a dental handpiece removably mounted at a first end thereof to the coupling component;
   c. an electrical generator mounted within the coupling component;
   d. a turbine wheel mechanically assembled to the electrical generator for causing the electrical generator to rotate when the turbine wheel rotates;
   e. a pressurized supply tube within the coupling component for conducting the pressurized fluid in a first direction from the supply hose first to drive a dental tool held in the handpiece at a second end thereof;
   f. an exhaust tube within the coupling component for conducting the pressurized fluid in a second direction to drive the turbine wheel within the coupling;
   g. a light source located within the coupling and electrically connected to the electrical generator to produce illumination when the electrical generator is rotated to generate an electrical current; and
   h. means within the dental handpiece for conveying illumination from the light source in the coupling to a position adjacent to the second end of the handpiece to illuminate the dental work site.

2. The dental work site illumination system described in claim 1, wherein the pressurized fluid is compressed air.

3. The dental work site illumination system described in claim 2, wherein the compressed air is exhaust compressed air subsequent to driving the dental tool.

4. The dental work site illumination system described in claim 1, further comprising a pressurized supply tube mounted within the coupling component, the pressurized supply tube having an input end and an output end, the input end positioned to receive a flow of pressurized fluid from the supply hose and the output end positioned to deliver the flow of pressurized fluid to the dental handpiece.

5. The dental work site illumination system described in claim 4, wherein the exhaust tube is mounted within the coupling component, the exhaust tube having an input end and an output end, the input end positioned to receive a flow of exhaust fluid from the dental handpiece and the output end positioned to deliver the flow of exhaust fluid to drive the turbine wheel.

6. The dental work site illumination system described in claim 1, wherein the light source is an LED light source.

7. The dental work site illumination system described in claim 1, wherein the turbine wheel is formed with a plurality of angularly oriented vanes.

8. A dental work site illumination system, comprising:
   a. an electrical generator residing within a dental coupling, a first end of the dental coupling mounted to a pressurized fluid supply hose and a second end of the dental coupling mounted to a dental handpiece;
   b. a light source residing within the dental coupling, the light source in electrical communication with the electrical generator; and
   c. means for conveying light emanating from the light source, the means extending from a first end thereof adjacent to the light source and passing through the handpiece to a second end adjacent to a dental work site.

9. The dental work site illumination system described in claim 8, wherein the pressurized fluid is pressurized air.

10. The dental work site illumination system described in claim 9, wherein the pressurized air is exhaust air.

11. The dental work site illumination system described in claim 8, wherein the means for conveying light comprises a fiber optic bundle.

12. The dental work site illumination system described in claim 8, further comprising a turbine wheel mechanically connected to the electrical generator and positioned for being driven by the pressurized fluid.

13. The dental work site illumination system described in claim 12, wherein the pressurized fluid is exhaust pressurized fluid subsequent to driving a dental tool.

14. The dental work site illumination system described in claim 8, wherein the light source is an LED light source.

15. The dental work site illumination system described in claim 8, wherein the electric generator is made of materials adapted to undergo repeated autoclave cycles.

16. The dental work site illumination system described in claim 1, wherein the pressurized fluid is exhaust pressurized fluid subsequent to driving a dental tool.

17. A dental work site illumination system, comprising:
  a. a coupling component assembled at a first end thereof to a supply hose, the supply hose configured for conveying pressurized fluid to the coupling component;
  b. a dental handpiece removably mounted to the coupling component at a second end thereof;
  c. an electrical generator mounted within the coupling component;
  d. a turbine wheel mechanically assembled to the electrical generator for causing the electrical generator to rotate when the turbine wheel rotates;
  e. a light source residing within the coupling, the light source electrically connected to the generator;
  f. means extending from the light source within the coupling to a lens located adjacent to a dental work site;
  g. a first tube connected at a first end thereof to the supply hose and passing through the handpiece to a second end adjacent to the dental work site in order for the pressurized fluid to drive a dental tool; and
  f. a second tube having a first end positioned adjacent to the dental tool and a second end positioned for delivering exhaust pressurized fluid to drive the turbine wheel;
  g. whereas the pressurized fluid first drives the dental tool and the exhaust pressurized fluid subsequently drives the turbine wheel.

18. The dental work site illumination system described in claim 17, wherein the light source is an LED light source.

19. The dental work site illumination system described in claim 17, wherein the means for conveying light comprises a fiber optic bundle.

20. The dental work site illumination system described in claim 17, wherein the turbine wheel is formed with a plurality of angularly oriented vanes.

* * * * *